(12) United States Patent
Girotti et al.

(10) Patent No.: US 7,812,204 B2
(45) Date of Patent: Oct. 12, 2010

(54) PROCESS FOR THE PRODUCTION OF 2,6-DIMETHYLNAPHTHALENE

(75) Inventors: Gianni Girotti, Novara (IT); Franco Rivetti, Milan (IT); Renzo Bignazzi, Legnano-Milano (IT)

(73) Assignee: Polimeri Europa S.p.A., Brindisi (IT)

( * ) Notice: Subject to any disclaimer, the term of this patent is extended or adjusted under 35 U.S.C. 154(b) by 865 days.

(21) Appl. No.: 11/576,412

(22) PCT Filed: Nov. 30, 2005

(86) PCT No.: PCT/EP2005/012951

§ 371 (c)(1),
(2), (4) Date: Mar. 30, 2007

(87) PCT Pub. No.: WO2006/069615

PCT Pub. Date: Jul. 6, 2006

(65) Prior Publication Data

US 2007/0265480 A1    Nov. 15, 2007

(30) Foreign Application Priority Data

Dec. 29, 2004 (IT) .................. MI2004A2537

(51) Int. Cl.
C07C 5/27 (2006.01)
C07C 6/12 (2006.01)
C07C 2/64 (2006.01)

(52) U.S. Cl. .......... 585/320; 585/481; 585/475; 585/467

(58) Field of Classification Search ........... 585/320, 585/481, 475, 467
See application file for complete search history.

(56) References Cited

U.S. PATENT DOCUMENTS

2003/0069459 A1   4/2003   Girotti et al.
2003/0144564 A1   7/2003   Pazzuconi et al.

Primary Examiner—Thuan Dinh Dang
(74) Attorney, Agent, or Firm—Oblon, Spivak, McClelland, Maier & Neustadt, L.L.P.

(57) ABSTRACT

The invention relates to a multi-step chemical transformation process for the production of 2,6-dimethylnaphthalene starting from one or more naphthalene hydrocarbons or hydrocarbon blends containing the same, one or more benzene hydrocarbons and, optionally, a methylating agent reacted in the presence of a catalyst containing a zeolite belonging to the MTW structural group, where hydrogen is fed in at least one of the steps.

68 Claims, 1 Drawing Sheet

PROCESS FOR THE PRODUCTION OF 2,6-DIMETHYLNAPHTHALENE

Figure 1:
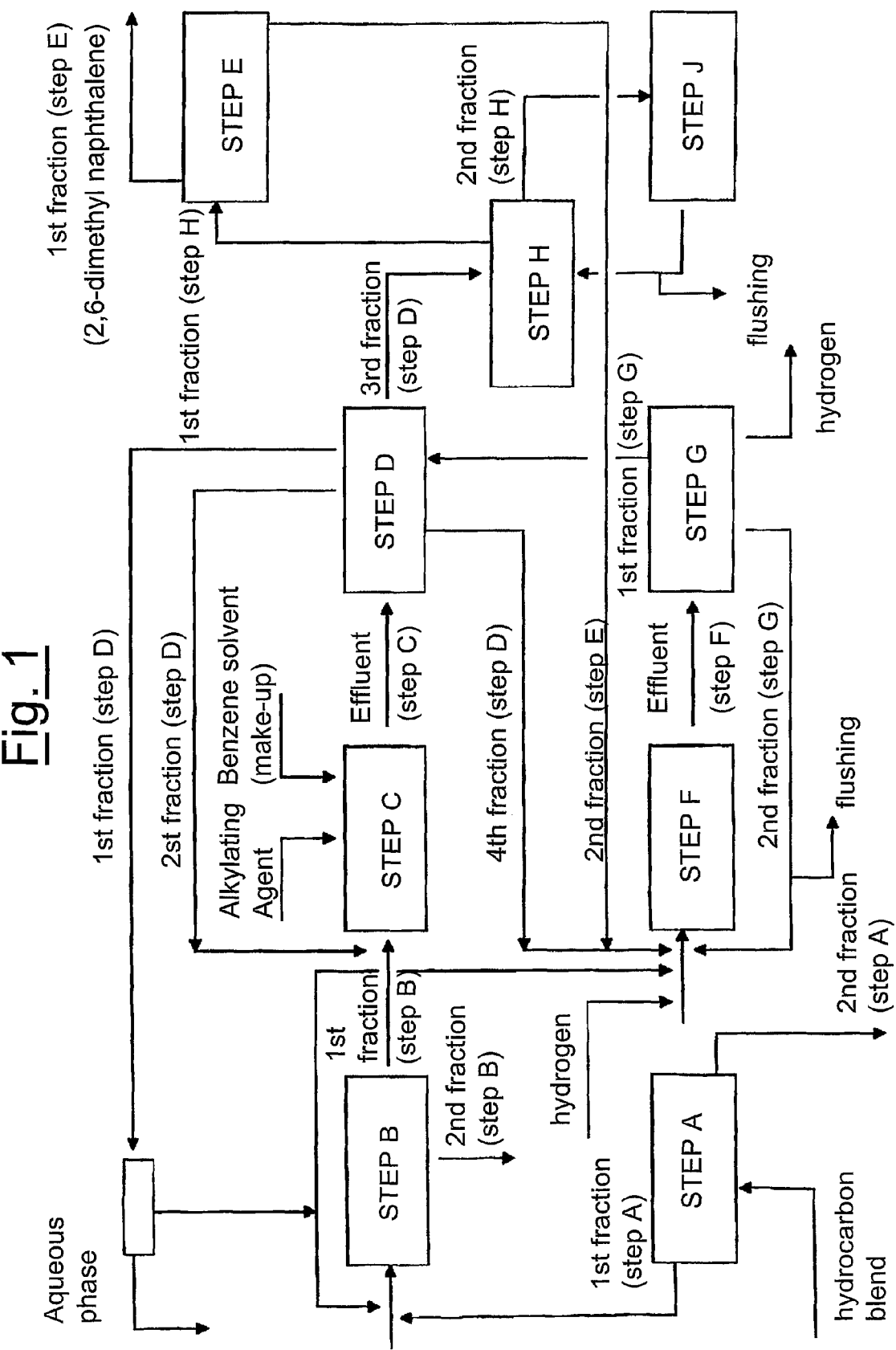

The present invention relates to a process for the production of 2,6-dimethylnaphthalene.

More specifically, the invention relates to a multi-step chemical transformation process for the production of 2,6-dimethylnaphthalene starting from one or more naphthalene hydrocarbons or hydrocarbon blends containing the same, one or more benzene hydrocarbons and, optionally, a methylating agent, reacted in the presence of a catalyst containing a zeolite belonging to the MTW structural group, where hydrogen is fed in at least one of the steps.

The naphthalene hydrocarbon can be selected from naphthalene, methyl naphthalene isomers, dimethyl naphthalene isomers, polymethyl naphthalene isomers and blends thereof.

Hydrocarbon blends are preferably used, containing naphthalene hydrocarbons, deriving from the fractionation of petrochemical or refinery streams.

The benzene hydrocarbon can be selected from benzene, toluene, xylene isomers, trimethyl-benzene isomers, tetramethyl benzene isomers, pentamethyl benzene, hexamethyl benzene and blends thereof. The methylating agent, if present, is preferably methanol.

The catalyst is preferably a ZSM-12 zeolite, in its acidic form and can additionally contain an inorganic binder.

The process is carried out in various chemical transformation steps effected in reactors, or groups of reactors, specifically dedicated to each of the above-mentioned steps.

Separation steps of the different effluents, effected by means of distillation and crystallization operations, are also associated with the chemical transformation steps.

2,6-dimethylnaphthalene is an intermediate product in the synthesis of 2,6-naphthalene dicarboxylic acid (or the corresponding dimethyl ester), used as monomer for the preparation of polyethylene naphthalate (PEN), a high performance polyester obtained by condensation of the acid with ethylene glycol.

PEN has several uses which mainly include the manufacturing of recyclable bottles for food products, heat-resistant containers for food products, high quality videotapes, advanced photographic applications and components for the production of tyres.

The particular and specific properties of PEN manufactured products mainly consist of high mechanical resistance, high thermal resistance and optimum gas-barrier properties (oxygen and carbon dioxide).

PEN applications are currently limited by the reduced availability and consequently high cost of 2,6-dimethylnaphthalene, which is produced starting from o-xylene and butadiene according to an onerous process from an economical point of view and characterized by numerous steps, as described in U.S. Pat. No. 4,990,717.

The first step of the process described in U.S. Pat. No. 4,990,717, includes the preparation of 5-(o-tolyl)-pentene-2 through the alkynylation of o-xylene with butadiene in the presence of a catalyst. The second step includes the preparation of 1,5-dimethyl tetraline by the cyclization of 5-(o-tolyl)-pentene-2 in the presence of a catalyst. The third step includes the preparation of 1,5-dimethyl naphthalene by the dehydrogenation of 1,5-dimethyl tetraline in the presence of a catalyst. The fourth step includes the preparation of a blend of dimethyl naphthalenes enriched in the 2,6-dimethylnaphthalene isomer by the isomerization of 1,5-dimethyl naphthalene in the presence of a catalyst. The process then comprises all the necessary purification steps, including that for obtaining the 2,6-dimethylnaphthalene isomer.

This process consequently has several drawbacks, among which a high cost of the raw materials, very high investment costs and also high production costs.

There are numerous alternative processes described in state of the art for the production of 2,6-dimethylnaphthalene.

The preparation of 2,6-dimethylnaphthalene effected according to what is described in U.S. Pat. No. 6,147,270, U.S. Pat. No. 6,232,517, U.S. Pat. No. 6,388,158, U.S. Pat. No. 6,737,558, and patent applications US 2003/0069459 and US 2003/00144564, is particularly suitable and consequently the descriptions of the above documents represent an integral part of the present patent application, to which reference is made for the description of the state of the art.

In accordance with what is described in said patents and patent applications, 2,6-dimethylnaphthalene is produced starting from one or more naphthalene hydrocarbons such as naphthalene, methyl naphthalene isomers, dimethyl naphthalene isomers, polymethyl naphthalene isomers, or starting from hydrocarbon blends obtained from the fractionation of petrochemical streams containing the same, which are reacted with one or more benzene hydrocarbons such as benzene, toluene, xylene isomers, trimethyl benzene isomers, tetramethyl benzene isomers, pentamethyl benzene, hexamethyl benzene and, optionally, with a methylating agent, for example, methanol, in the presence of a catalyst containing a zeolite belonging to the MTW structural group, such as, preferably, ZSM-12.

This process is completely different from the process of the known art: it is, in fact, the result of transalkylation, isomerization and alkylation reactions in which all the methyl groups present in the reaction blend, both those present on the naphthalene hydrocarbons, and those present on the benzene hydrocarbons, as well as the methyl groups possibly introduced with the methylating agent, usefully take part. The intervention of the benzene hydrocarbon in these reactions, as donor or acceptor of methyl groups provides an essential contribution to the dynamic and performance of the process. In accordance with the above, at the end of the process, the hydrocarbon or blend of benzene hydrocarbons originates a different hydrocarbon or blend of benzene hydrocarbons, methylated in a different way and extent, both qualitatively and quantitatively.

In industrial practice, a suitable use of the methylating agent allows the quantitative restoration, in the hydrocarbon or blend of benzene hydrocarbons, of the initial content of methyl groups, so that the benzene hydrocarbon is not substantially used up during the entire process and does not therefore represent a reagent, but a sort of "reactive solvent" which, although actively and essentially participating in the chemical reactions, does not need to be restored through the addition of fresh raw material, except for the re-establishment of small quantities of the solvent itself, when this contains, after the long use, impurities which are difficult to separate and can therefore be conveniently removed through purging operations of the solvent itself.

In patent application US 2003/0069459 this preparation process of 2,6-dimethylnaphthalene is effected, in particular, by means of the combination of several chemical transformation steps, associated both with separation steps through the distillation of the effluents from said chemical transformation steps, and with purification steps through crystallization. Running the process in separate chemical transformation steps, each of which characterized by specific reactants and products, maximizes the overall production of 2,6-dimethylnaphthalene. In the chemical transformation first step, in addition to the naphthalene component, a methylating agent is optionally used, for example methanol, together with a benzene hydrocarbon or a blend of benzene hydrocarbons, wherein the overall ratio between the number of benzene methyl moles and the number of moles of benzene aromatic rings is preferably equal to or higher than 2. The overall composition of the reagent blend used in the first chemical transformation step, together with the catalyst and the reaction conditions, give a product in which the naphthalene fraction is characterized by an overall ratio between the number of moles of methyl radicals and the number of moles of naphthalene rings, which is higher than that of the starting naphthalene fraction reacted. In the first chemical transformation step, therefore, a series of chemical transalkylation reactions takes place, and, possibly alkylation between the benzene molecules, the naphthalene molecules and the molecules of the possible methylating agent. In this first chemical transformation step, the production of dimethyl naphthalene isomers, among which the 2,6-dimethylnaphthalene isomer, is effected.

In the second chemical transformation step, in addition to the naphthalene component, a hydrocarbon or a blend of benzene hydrocarbons is used, whose overall ratio between the number of moles of benzene methyls and the number of moles of benzene aromatic rings is preferably lower than 2. The overall composition of the reagent mix used in the second chemical transformation step, together with the catalyst and the reaction conditions, give a product in which the naphthalene fraction is characterized by an overall ratio between the number of moles of methyl radicals and the number of moles of naphthalene rings lower than that of the starting naphthalene fraction reacted. In the second chemical transformation step, a series of transalkylation chemical reactions takes place between the benzene and the naphthalene molecules. The production of naphthalene and monomethyl naphthalenes takes place in this second chemical transformation step, to the detriment of the heavier isomers.

The naphthalene and monomethyl naphthalenes produced in this second chemical transformation step are then usefully recycled to the first chemical transformation step previously described.

In a third chemical transformation step, by operating according to a particular embodiment of the process described in US 2003/0069459, an additional production of the 2,6-dimethylnaphthalene isomer is obtained, to the detriment of other dimethyl naphthalene isomers, in particular to the detriment of 1,5 and 1,6-dimethyl naphthalene isomers. In this step, no benzene hydrocarbon is used in addition to the naphthalene fraction having the above-mentioned chemical composition. Thanks to the reagent typology used, together with the catalyst and the reaction conditions, in this third step, mainly isomerization chemical reactions take place between the different naphthalene molecules, so as to maintain the overall ratio between the number of moles of methyl radicals and the number of moles of naphthalene rings with respect to that of the reagent, practically unaltered in the products. In this chemical transformation third step, therefore, an additional production of the 2,6-dimethylnaphthalene isomer is obtained, to the detriment of other dimethyl naphthalenes isomers, in particular to the detriment of 1,5- and 1,6-dimethyl naphthalene isomers.

The use of more independent chemical transformation steps, as described in US 2003/0069459 allows the overall yield to 2,6-dimethylnaphthalene of the process to be maximized, thanks to the high selectivity to 2,6-dimethylnaphthalene reached in the first chemical transformation step and to the recovery of the by-products effected in the second and possibly in third chemical transformation step. The first chemical transformation step, effected as described above, allows a selectivity to 2,6-dimethylnaphthalene to be obtained, which is much higher than what is expected from the thermodynamic equilibrium, associated with a selectivity towards the 1,6-dimethyl naphthalene and 1,5-dimethyl naphthalene isomers, which can easily be isomerized to the desired 2,6-dimethylnaphthalene isomer, also higher than what is expected from the thermodynamic equilibrium, with a consequent simplification and economical benefit for the process. The second chemical transformation step, effected according to what is described above, allows the recovery of the naphthalene hydrocarbons reacted, by means of their transformation into naphthalene and monomethyl naphthalene isomers, which are therefore usefully recycled to the first chemical transformation step. The third chemical transformation step, effected according to a particular embodiment of the invention as previously described, allows a further recovery of the naphthalene hydrocarbons reacted, producing an additional amount of the desired product 2,6-dimethylnaphthalene with respect to that already produced in the first step of the chemical transformation.

The process described allows excellent results to be obtained in terms of yield, selectivity, conversion, productivity and catalyst life, higher than that described in the previous art. In addition, the process described allows the production of 2,6-dimethylnaphthalene starting from petrochemical or refinery cuts, of low value and difficult to sell on the market, containing variable amounts of naphthalene hydrocarbons, among which naphthalene, monomethyl naphthalenes, dimethyl naphthalenes, polymethyl naphthalenes, in any relative percentage composition with each other, with a consequent further economical benefit for the process.

The process described in US 2003/0069459, however, preferably requires the use, in reaction, of large amounts of hydrocarbon or blends of benzene hydrocarbons, in relation to the hydrocarbon or blend of naphthalene hydrocarbons reacted in the first and second chemical transformation step. As shown, in fact, in the descriptive examples of the process in the patents cited above, a molar ratio between the hydrocarbon or blend of benzene hydrocarbons and the hydrocarbon or blend of naphthalene hydrocarbons, is practically used, which can reach a value of 18. This means a higher cost in the industrial embodiment of the process due to the larger dimensions required for the reactors of the first and second chemical transformation step and for the separation equipment required downstream of said reactors, as well as for the higher energy cost required for the separations and inner recycling to the process.

By operating according to the above-mentioned process, on the other hand, if, in order to reduce costs, the molar ratio is reduced between the hydrocarbon or blend of benzene hydrocarbons used in the reaction, undesired impurities are observed, due to condensation reactions between the naphthalene molecules and/or due to a partial degradation of the reactive solvent, with a consequent higher cost for the restoration of the same.

It has now been found, and this represents an object of the present invention, that it is possible to effect the process described above, also using a reduced molar ratio between the hydrocarbon or blend of benzene hydrocarbons and the naphthalene reagent, even in the order of 5 or less, without having the consequences described above, when operating in the presence of hydrogen, together with the reactants, in the first and/or second chemical transformation step.

According to a preferred embodiment of the invention, hydrogen is used, at least in the second chemical transformation step of the process.

By operating in the presence of hydrogen, according to the process of the present invention, optimum yields are obtained at low values of the benzene hydrocarbon/naphthalene hydrocarbon ratio, increases in flushings or amounts of fresh raw materials to be reintegrated are not required, and a decrease in the catalyst life is not observed over a long period of time.

An object of the present invention therefore relates to a process for the production of 2,6-dimethylnaphthalene starting from hydrocarbon blends containing naphthalene and/or methyl naphthalene isomers and/or dimethyl naphthalene isomers and/or polymethyl naphthalene isomers, one or more benzene hydrocarbons, optionally a methylating agent, in the presence of a zeolite catalyst belonging to the MTW structural group, comprising the following steps:

I. A first chemical transformation I of naphthalene blends containing naphthalene and/or methyl naphthalene isomers and/or dimethyl naphthalene isomers and/or polymethyl naphthalene isomers, effected in the presence of one or more benzene hydrocarbons, a catalyst containing a zeolite belonging to the MTW structural group, optionally a methylating agent, with the aim of producing a naphthalene blend enriched in the 2,6-dimethylnaphthalene isomer, wherein the benzene hydrocarbon is selected from benzene, toluene, xylene isomers, trimethyl benzene isomers, tetramethyl benzene isomers, pentamethyl benzene, hexamethyl benzene and blends thereof, and the overall ratio between the number of moles of methyl radicals contained in the benzene hydrocarbons and the number of moles of benzene rings is higher than the overall ratio between the number of moles of methyl radicals contained in the naphthene hydrocarbons and the number of moles of naphthalene rings of the naphthalene fraction reacted, II. A second chemical transformation II of naphthalene blends mainly containing dimethyl naphthalene isomers and/or polymethyl naphthalene isomers, effected in the presence of a catalyst containing a zeolite belonging to the MTW structural group, and one or more benzene hydrocarbons selected from benzene, toluene, xylene isomers, trimethyl benzene isomers, tetramethyl benzene isomers, pentamethyl benzene, hexamethyl benzene and blends thereof, and the overall ratio between the number of moles of methyl radicals contained in the benzene hydrocarbons and the number of moles of benzene aromatic rings is lower than the overall ratio between the number of moles of methyl radicals contained in the naphthene substrate and the number of moles of naphthalene rings of the naphthalene fraction reacted, with the aim of obtaining a naphthalene blend containing a higher concentration of naphthalene and methyl naphthalenes with respect to the blend reacted, wherein said naphthalene and methyl naphthalenes are re-used in step I;

III. Optionally a third chemical transformation III of naphthalene blends mainly containing dimethyl naphthalene isomers, effected in the absence of benzene hydrocarbons and in the presence of a catalyst containing a zeolite belonging to the MTW structural, with the aim of obtaining a blend of dimethyl naphthalene isomers, enriched in the 2,6-dimethylnaphthalene isomer, wherein hydrogen is fed in the chemical transformation step I and/or in the chemical transformation step II.

Obviously, in step I benzene can only be used in a mixture with at least one other methylated benzene hydrocarbon.

The process of the present invention can contain at least one separation step, by distillation, of the blends resulting from the chemical transformations and at least one purification phase, by means of crystallization operations and washings, of the blends resulting from the chemical transformations.

In particular, the naphthalene blend resulting from the chemical transformation I is subjected to one or more separation steps, obtaining several fractions, among which a fraction with a higher concentration of the 2,6-dimethylnaphthalene isomer, possibly a fraction with a higher concentration of 1,6 and 1,5-dimethyl naphthalene isomers, to be used for feeding step III, and at least a fraction containing mainly dimethyl naphthalenes and/or polymethyl naphthalenes to be used for feeding step II.

The naphthalene blend obtained from the chemical transformation II is subjected to one or more separation steps, obtaining several fractions, among which a fraction containing naphthalene and methyl naphthalene, which is sent to step I.

According to a preferred embodiment of the invention, hydrogen is used at least in step II of the chemical transformation process.

In step I the naphthalene hydrocarbon can be selected from methyl naphthalene, dimethyl naphthalene isomers, trimethyl naphthalene isomers, tetramethyl naphthalene isomers, pentamethyl naphthalene isomers, hexamethyl naphthalene isomers and blends thereof, and, according to a particularly preferred aspect, the naphthalene hydrocarbon blend used mainly contains naphthalene and monomethyl naphthalene.

The benzene hydrocarbon is preferably introduced into the process in the form of toluene, xylene or 1,2,4-trimethyl benzene, also called "pseudo-cumene" or blends thereof.

The hydrocarbon or the benzene hydrocarbon blend introduced into the chemical transformation step I, preferably presents an overall ratio between the number of moles of methyl radicals contained in the benzene aromatic hydrocarbons and the number of moles of benzene aromatic rings equal to or higher than 2.

In the chemical transformation step II, the hydrocarbon or benzene hydrocarbon blend preferably has an overall ratio between the number of moles of methyl radicals contained in the benzene aromatic hydrocarbons and the number of moles of benzene aromatic rings equal to or lower than 2.

According to a preferred embodiment of the process, the chemical transformation step I is effected in the presence of a methylating agent. The methylating agent is selected from methanol, dimethyl ether, dimethyl carbonate, dimethyl sulphate, methyl iodide. The methylating agent is preferably methanol.

The catalyst used in both the chemical transformation step II and in the chemical transformation step III, when the latter step is present, is a zeolite belonging to the MTW structural group (according to the IZA classification).

Zeolites of the MTW structural group which can be used are, for example, ZSM-12, CZH-5, Nu-13, Theta-3, TPZ-12, VS-12.

ZSM-12 zeolite is described in U.S. Pat. No. 3,832,449, Zeolites, 5, 346-348 (1985) and in J. Phys. Chem., 94, 3718-3721 (1990).

CZH-5 zeolite is described in GB 2079735A. NU-13 zeolite is described in EP 59059. Theta-3 zeolite is described in Ep 162719. TPZ-12 zeolite is described in U.S. Pat. No. 4,557,919. Vs-12 zeolite is described in Chem. Commun., 1491-1492 (1994).

The zeolite of the MTW structural group which is most suitable for being used in the present invention, is a silico-aluminate having an $SiO_2/Al_2O_3$ molar ratio higher than or equal to 20 and preferably higher than 70. This zeolite and its preparation are described in Chem. Ind. (Dekker) (Synthesis of Porous Materials) 69, 127-137 (1997). The aluminum can be totally or partially substituted with B, Ga, Fe or mixtures thereof, as described by Toktarev and Ione in Progress in Zeolites and Microporous Materials, SSSC, vol. 105 (1997).

The catalyst preferably includes a ZSM-12 zeolite which has, in its calcined and anhydrous form, a molar composition of oxides corresponding to the formula

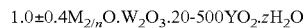

$$1.0 \pm 0.4 M_{2/n}O \cdot W_2O_3 \cdot 20\text{-}500 YO_2 \cdot zH_2O$$

wherein M is $H_+$ and/or an alkaline or alkaline earth metal having a valence n, W is selected from aluminum, gallium or mixtures thereof, Y is selected from silicon and germanium, z is between 0 and 60. M is preferably selected from sodium, potassium or mixtures thereof. W is preferably aluminum and Y is preferably silicon. W can be substituted, at least partially, with boron, iron or mixtures thereof.

According to a particularly preferred aspect, the MTW zeolite is used in the form in which the cationic sites present in its structure are occupied, at least for 50%, by acidic hydrogen ions, more preferably for at least 90%.

The zeolite can be used as such, or obtained in the form of pellets by means of extrusion, or obtained in the form of micro-spheres by means of spray-drying, as such or mixed with a suitable inorganic binder. The binder can be, for example, alumina, silica, a silico-aluminate, titania, zirconia or clay. The binder is preferably alumina. In the bound catalyst, the zeolite and binder can be in a weight ratio ranging from 5/95 to 95/5, preferably from 20/80 to 80/20.

In a preferred form, the finished catalyst is also characterized by particular characteristics of extra-zeolite porosity, i.e. the porosity fraction of the catalyst which cannot be attributed to the amount and quality of the zeolite present in the finished catalyst. In particular, said extra-zeolite porosity has values not lower than 0.4 ml/g of finished catalyst associated with a fraction equal to at least 50% of said extra-zeolite porosity characterized by pores having a diameter higher than 100 Angstrom. Said extra-zeolite porosity can be obtained through conventional preparation methods and is correctly determined according to the known methods described, for example, in Loweel, Seymour "Introduction to powder surface area", Wiley Interscience.

The MTW zeolites which are used in steps I, II and III, are independently selected and can be different, both qualitatively and quantitatively, as far as the chemical composition is concerned.

The molar ratio used in the chemical transformation steps I and/or II, between the hydrocarbon or the blend of benzene hydrocarbons and the hydrocarbon or the blend of naphthalene hydrocarbons, when step I and/or step II are effected in the presence of hydrogen, preferably ranges from 1 to 10, even more preferably from 1 to 5. According to a particularly preferred aspect, said ratio is higher than or equal to 2 and lower than 5.

When step I or step II are effected in the absence of hydrogen, a molar ratio between the benzene hydrocarbon and the naphthalene hydrocarbon, higher than 5 and lower than 20, is preferably used.

When the process according to the invention is effected in the presence of a methylating agent in the chemical transformation step I, the molar ratio used between the methylating agent and the hydrocarbon or the blend of naphthalene hydrocarbons is lower than 30, and generally ranges from 0.1 to 3.

The reaction temperatures adopted in chemical transformation steps I, II and III are selected independently and can vary within the range of 150° C. to 450° C.

The pressures which can be used in chemical transformation steps I, II and III are selected independently and can vary within the range of 3 to 60 absolute bar.

The combination of the temperature and pressure conditions independently adopted in chemical transformation steps I, II and III is preferably selected so that each chemical transformation is run at least partially, in liquid phase and more preferably under completely liquid phase conditions.

The molar ratios used in the chemical transformation steps I and/or II between hydrogen and the hydrocarbon or the blend of naphthalene hydrocarbons are independent of one another and range from 0.1 to 100, preferably from 0.5 to 10. The purity of the hydrogen used is not particularly critical and the hydrogen can contain, for example, up to 5% by volume of carbon monoxide. According to an aspect of the invention, the non-reacted hydrogen, after separation from the other components of the effluent mix from the chemical transformation steps I and II, is separated and re-used in the recycling to feed the step or steps which include its use, preferably the chemical transformation step of origin.

The chemical transformation steps I, II and III contained in the process, object of the present invention can be carried out, independently of each other, batchwise, in semi-continuous or in continuous, but they are preferably effected in continuous. The chemical transformation steps I, II and III are preferably carried out in fixed bed reactors, containing one or more catalytic beds between which a suitable fraction of the overall quantity of reactants fed to the reactor, is fed. The reactants can be fed to the reactor, in the desired proportions, all at the beginning of the reactor or at the first catalytic bed, or the feeding of the reactants or some of them can be partialized in two or more steps along the reactor or at the various catalytic beds.

In a particularly preferred embodiment, with reference to the chemical transformation step I, 4 reaction steps are adopted in series, to the first of which all the hydrocarbon or blend of benzene hydrocarbons, and optionally hydrogen when present, are fed, according to the reaction conditions selected, together with a first portion of the hydrocarbon or blend of naphthalene hydrocarbons, the remaining portions of hydrocarbon or blend of naphthalene hydrocarbons are fed to the second or third step, whereas the whole quantity of methylating agent envisaged is fed to the fourth step.

In this case, the weigh hourly space velocity, WHSV, expressed in kg of charge fed/hour/kg of overall catalyst present in the four reaction steps, ranges from 0.1 to 8 $\text{hours}^{-1}$, preferably from 0.5 to 4 $\text{hours}^{-1}$.

In a particularly preferred embodiment, with reference to the chemical transformation step II, 4 reaction step are adopted in series, to the first of which all the hydrocarbon or blend of benzene hydrocarbons, and hydrogen when present, are fed, according to the reaction conditions selected, together with a first portion of the hydrocarbon or blend of naphthalene hydrocarbons, whereas the remaining portions of hydrocarbon or blend of naphthalene hydrocarbons are fed to the remaining catalytic steps. The above four reaction steps, with reference to both the chemical transformation step I and chemical transformation step II, can be effected inside a single reactor containing the catalyst arranged in four distinct fixed beds or by means of four reactors in series.

By operating according to the invention, the catalyst used in the chemical transformation steps I, II and III can normally be adopted for long periods of time before showing signs of deactivation, the catalyst, however, can be subjected, if necessary, to regeneration treatment to reestablish the original performances.

The most suitable method is by combustion of the carbonaceous deposits accumulated in the period of use, according to what is known in the state of the art, operating, for example, at a temperature ranging from 450 to 550° C., at a pressure ranging from 1 to 3 bar, with mixtures of oxygen and nitrogen in a ratio ranging from 0.1 to 20% by volume and with a space velocity (GHSV=Gas Hourly Space Velocity), expressed in l of gas mixture/hour/l of catalyst) ranging from 3000 to 6000 hours$^{-1}$. Said regeneration procedure can be carried out with the in-situ procedure, or with the ex-situ procedure, i.e. by unloading the catalyst during the periodical maintenance phases of the plant to be regenerated elsewhere; in this way, the reactor can be constructed without the control devices necessary for carrying out the regeneration.

A further method suitable for the regeneration of the catalyst consists in treating the exhausted catalyst under at least partially liquid phase conditions, preferably under totally liquid phase conditions, with one or more benzene hydrocarbons, such as benzene, toluene, xylene isomers, trimethylbenzene isomers, tetramethylbenzene isomers, pentamethylbenzene, hexamethylbenzene, at a temperature ranging from 200° C. to 450° C., preferably from 300° C. to 400° C., and at least equal to the temperature used in the specific chemical transformation step in which the catalyst left to regenerate has been used, at a pressure ranging from 3 to 60 absolute bar and at a WHSV, as defined above, ranging from 0.1 to 8 hours$^{-1}$, preferably from 0.5 to 4 hours$^{-1}$. The treatment is preferably carried out in-situ, i.e. directly on the catalyst contained in the reactor or in the reactors of each chemical transformation step. The hydrocarbon or blend of benzene hydrocarbons preferably used in the regeneration, is the same as that already adopted during the running of the reactor, when present.

According to an aspect of the invention, in the present preparation process of 2,6-dimethylnaphthalene, hydrocarbon blends are used as feeding to step I, containing naphthalene hydrocarbons deriving from the fractionation of petrochemical or refinery streams, such as those obtained by the distillation of cracking oils called FOK (Fuel Oil Cracking, otherwise known as Steam Cracking Cycle Oil), coming from Steam Cracking operations for the transformation of naphtha into light olefins and LCO (Light Cycle Oil), coming from FCC (Fluid Catalytic Cracking) of petroleum. These distillation cuts preferably contain at least 20% by weight of naphthalene derivatives.

According to a further aspect of the invention, said hydrocarbon blends containing varying quantities of naphthalene compounds, in particular FOK and LCO, are previously subjected to a pre-treatment step before being fed to step I of the process. The pre-treatment comprises a first concentration step A of the naphthalene component present in the above hydrocarbon blends by means of distillation, followed by a purification step B from the impurities present by treatment with a solid acid catalyst. As far as the purification step B is concerned, this is effected in continuous, semi-continuous or batchwise, preferably in continuous, by feeding the concentrated naphthalene stream to a reactor containing the solid acid catalyst. The step is carried out under at least partially liquid phase conditions, preferably under liquid phase conditions, at a temperature ranging from room temperature to 360° C. If the operation is carried out batchwise or in semi-continuous, the quantity of acid solid generally varies from 0.1% to 5% by weight with respect to the hydrocarbon blend to be treated coming from step A, for a treatment time not longer than 5 minutes. If the operation is carried out in continuous, the hydrocarbon blend coming from step A is fed to step B with a WHSV ranging from 0.1 to 6 hours$^{-1}$. According to an aspect of the invention, the concentrated naphthalene stream is fed to the treatment after dilution with one or more benzene hydrocarbons, such as benzene, toluene, xylene isomers, trimethylbenzene isomers, tetramethylbenzene isomers, pentamethylbenzene, hexamethylbenzene.

According to a further aspect, the effluent from the treatment on the acid solid is subjected to distillation to obtain a purified naphthalene stream, optionally diluted in the hydrocarbon or blend of benzene hydrocarbons, and a heavier non-naphthalene stream.

Acid solid materials suitable for the purposes of the invention are, for example, clays (montmorillonites, smectites), phyllo-silicates, acid or partially acid zeolites, sulfated zirconia, acid resins such as sulfonic resins or styrene-divinylbenzene copolymers functionalized with sulfonic groups, alumina (optionally chlorinated or fluorinated), activated aluminas, amorphous silico-aluminas, acid oxides in general. Heteropoly acids, salified heteropoly acids (with Cs or other metals) and supported acids such as phosphoric acid on kieselguhr or other natural or synthetic carriers, can also be used.

Using the hydrocarbon blends obtained at the end of the treatment described above as feeding to step I of the chemical transformation process, is a preferred aspect of the present invention.

In accordance with what is specified above, a particular object of the present invention relates to an integrated process containing the following steps and in which hydrogen is fed to step C and/or step F:

A. Separation by distillation of a hydrocarbon blend, containing, among other products, naphthalene and/or methylnaphthalene isomers and/or dimethylnaphthalene isomers and/or polymethylnaphthalene isomers in order to obtain a first hydrocarbon fraction characterized by a higher concentration of naphthalene compounds with respect to the initial hydrocarbon blend and a second fraction prevalently consisting of non-naphthalene compounds, wherein the first fraction is sent to the subsequent step B whereas the second fraction leaves the process;

B. Treatment of the first fraction obtained in step A by reaction of said fraction with a solid acid catalyst, optionally in the presence of a hydrocarbon or blend of benzene hydrocarbons, and separation by distillation of the hydrocarbon blend effluent from said treatment, in order to obtain a first hydrocarbon fraction consisting of said naphthalene compounds and possibly the hydrocarbon or blend of benzene hydrocarbons, sent to the subsequent step C, and a second hydrocarbon fraction prevalently containing heavy non-naphthalene compounds, which leaves the process;

C. Chemical transformation I of the first fraction obtained in step B and the second fraction obtained in step D, containing as a whole naphthalene and/or methylnaphthalene isomers and/or dimethylnaphthalene isomers and/or polymethylnaphthalene isomers, in a hydrocarbon blend effluent from said step C enriched with 2,6 dimethylnaphthalene isomer, wherein said chemical transformation I is carried out in the presence of one or more benzene hydrocarbons which have an overall ratio between the number of moles of methyl radicals contained in the aromatic benzene hydrocarbons and the number of moles of aromatic benzene rings preferably equal to or higher than 2, a solid acid catalyst containing a MTW zeolite, preferably ZSM-12, and an inorganic binder, and optionally in the presence of a methylating agent;

D Separation by distillation of the hydrocarbon blend effluent from step C and subsequent step G, containing an aqueous phase, one or more benzene hydrocarbons, naphthalene and/or methylnaphthalene isomers and/or dimethylnaphthalene isomers and/or polymethylnaphthalene isomers in order to obtain:

a first fraction prevalently consisting of water and a blend of benzene hydrocarbons prevalently containing benzene, toluene and xylenes have an overall molar ratio between methylbenzenes and benzene rings lower than or equal to 2, wherein said fraction, after separation and removal by demixing of the aqueous phase, is partly sent to step B and partly to the subsequent step F;

a second fraction prevalently consisting of (1) a hydrocarbon or blend of prevalently tri-, tetra-, penta-benzene hydrocarbons and hexamethylbenzene, and possibly xylenes, having an overall molar ratio between methylbenzenes and benzene rings higher than 2, 2) naphthalene, 3) methylnaphthalene isomers, wherein said second fraction is sent to the previous step C;

a third fraction prevalently consisting of dimethylnaphthalene isomers, including the 2,6 dimethylnaphthalene isomer, which is sent to the subsequent step H;

a fourth fraction prevalently consisting of tri-, tetra-, penta- and hexamethylnaphthalenes, which is sent to the subsequent step F;

E. Purification of the first fraction, obtained from the subsequent step H, and prevalently consisting of a blend of dimethylnaphthalene isomers characterized by a high concentration of the 2,6-dimethylnaphthalene isomer and a low concentration of the 1,6- and 1,5-dimethylnaphthalene isomers, by means of crystallization steps by cooling, subsequent washings and recrystallizations effected in the presence of a low molecular weight alcohol selected from methanol, ethanol and propanol, to obtain a first fraction consisting of 2,6-dimethylnaphthalene with a very high degree of purity, which forms the desired end-product, and a second fraction prevalently consisting of dimethylnaphthalene isomers, comprising the 2,6-dimethylnaphthalene isomer, wherein said second fraction obtained in the present step E is sent to the subsequent step F;

F. Chemical transformation II of the hydrocarbon blend prevalently containing dimethylnaphthalene isomers and/or polymethylnaphthalene isomers greater than dimethylnaphthalene, carried out in the presence of a solid acid catalyst, containing a MTW zeolite, preferably ZSM-12 zeolite, and an inorganic binder, and a hydrocarbon or blend of benzene hydrocarbons so that the overall molar ratio between the methylbenzenes and benzene rings is lower than or equal to 2, in order to obtain a hydrocarbon blend, effluent from said step F, having a higher concentration of naphthalene and methylnaphthalenes with respect to the total blend reacted, and wherein said blend is sent to the subsequent step G;

G. Separation by distillation of a hydrocarbon blend containing a hydrocarbon or blend of benzene hydrocarbons, naphthalene and/or methylnaphthalene isomers and/or dimethylnaphthalene isomers and/or polymethylnaphthalene isomers obtained in the previous step F, to obtain:

a first fraction consisting of a hydrocarbon or blend of benzene hydrocarbons, naphthalene and methylnaphthalene isomers, which is sent to the separation step D, a second fraction prevalently consisting of dimethylnaphthalene isomers, comprising the 2,6-dimethylnaphthalene isomer, and polymethylnaphthalenes, which is sent, totally or partially, to the chemical transformation step F;

H. Separation, by distillation, of a hydrocarbon blend prevalently consisting of dimethylnaphthalene isomers in order to obtain:

a first fraction prevalently consisting of dimethylnaphthalene isomers with a higher concentration of the 2,6-dimethylnaphthalene isomer and a lower concentration of 1,6- and 1,5-dimethylnaphthalene isomers, with respect to the initial concentrations of the mixture fed in the present step, which is sent to the previous step E;

a second fraction prevalently consisting of dimethylnaphthalene isomers with a lower concentration of the 2,6-dimethylnaphthalene isomer and a higher concentration of 1,6- and 1,5-dimethylnaphthalene isomers, with respect to the initial concentrations of the mixture fed in the present step, which is sent to the subsequent step J;

J. Chemical transformation III of a hydrocarbon blend prevalently consisting of dimethylnaphthalene, obtained as second fraction of the previous step H, carried out in the presence of a catalyst containing a MTW zeolite, preferably ZSM-12 zeolite, and an inorganic binder, in order to obtain a hydrocarbon blend, effluent of said step J, having a higher concentration of the 2,6-dimethylnaphthalene isomer with respect to the concentration of the mixture fed to said step J, which is totally or partially sent back to step H.

A particularly preferred aspect of the present invention is the integrated process described above wherein hydrogen is fed to step F only and this particular preferred embodiment, with the relative arrangement of the various chemical transformation steps and various separation steps, with the feeding of an alkylating agent in step C and with a fraction consisting of hydrogen leaving step G and being re-fed to step F, is represented in the scheme shown in FIG. 1.

The various steps forming the integrated process described above are each carried out adopting the generally conditions previously described for the relative chemical transformations I, II, III and for steps A and B. Further particular embodiment modes are described hereunder.

Step A, in which the hydrocarbon blend containing, among other products, naphthalene and/or methylnaphthalene isomers and/or dimethylnaphthalene isomers and/or polymethylnaphthalene isomers, is carried out using conventional distillation methods in order to obtain a hydrocarbon blend characterized by a concentration not lower than 20% of naphthalene compounds.

In step B, the hydrocarbon blend is fed, obtained in step A and containing, among other products, naphthalene and/or methylnaphthalene isomers and/or dimethylnaphthalene isomers and/or polymethylnaphthalene isomers, and preferably also a hydrocarbon fraction coming from step D and consisting of a hydrocarbon or blend of benzene hydrocarbons, prevalently benzene, toluene and xylenes, having an overall molar ratio between methyls and benzene rings lower than or equal to 2. Step B is carried out according to what has already been described in this patent application and according to U.S. Pat. No. 6,388,158.

The separation of the reaction effluent from step B into a first fraction consisting of a hydrocarbon or blend of benzene hydrocarbons and naphthalene compounds and into a second fraction containing heavy, non-naphthalene compounds is effected with conventional distillation methods.

Step C is carried out according to what has already been described for the chemical transformation I. When said chemical transformation is effected in the presence of hydrogen, it forms a new and further object of the present invention. Methanol is preferably used in step C as alkylating agent. If hydrogen is used in this step, the non-reacted hydrogen is separated in the subsequent step D.

The temperature at which the reaction in step C is carried out preferably ranges from 200° C. to 450° C., even more preferably from 300° C. to 400° C.

Step C can also envisage the feeding of an aliquot of hydrocarbon or blend of benzene hydrocarbons (FIG. 1, benzene solvent (make-up)), to compensate the losses observed during the process, preferably selected from toluene, xylene and trimethylbenzene or mixtures thereof.

Step F is carried out according to what has already been described for the chemical transformation II. The temperature at which the reaction in step F is effected preferably ranges from 200° C. to 450° C., even more preferably from 300° C. to 400° C.

Step J is carried out according to what has already been described for the chemical transformation III. The temperature at which the reaction in step J is effected preferably ranges from 150° C. to 400° C., even more preferably from 200° C. to 350° C.

The overall flow-rate of the reactants fed in steps C and/or F expressed as WHSV, ranges from 0.1 hours$^{-1}$ to 20 hours$^{-1}$ and preferably from 0.5 hours$^{-1}$ to 4 hours$^{-1}$.

The overall flow-rate of the reactants fed in steps J expressed as WHSV, ranges from 0.01 hours-1 to 20 hours$^{-1}$ and preferably from 4 hours$^{-1}$ to 16 hours$_{-1}$.

The pressure at which the reaction is carried out in steps C, J and F is selected from values which are such as to guarantee that the chemical transformation in each step takes place in at least partially liquid phase and preferably in completely liquid phase. The pressure is generally selected from 3 to 60 absolute bar.

The separation steps D, H and G, where the separation is effected of the various naphthalene fractions and hydrocarbon or blend of benzene hydrocarbons used together with the separation of the aqueous phase present from the organic phase, are carried out using conventional distillation and demixing methods by cooling.

Step E, wherein the separation and purification are effected of the 2,6-dimethylnaphthalene isomer from the mixture prevalently consisting of dimethylnaphthalene obtained from step H, is carried out as described in patent application U.S. Pat. No. 6,737,558. Step E comprises a crystallization step $E_a$ by cooling and the subsequent separation of the solid obtained, a step $E_b$ which comprises one or more washing phases and the subsequent separation of the solid obtained and a step $E_c$ which comprises a re-dissolution phase of the precipitate obtained in step $E_b$, a re-crystallization phase of the mixture thus obtained and the subsequent separation of the solid obtained. Said steps $E_a$, $E_b$ and $E_c$ are carried out in the presence of a low molecular weight alcohol selected from methanol, ethanol, propanol and glycols, preferably methanol.

The quantity of low molecular weight alcohol used in the crystallization phase $E_a$ by cooling in slurry under static conditions and/or under stirring or scraped surface crystallization ranges from 0.001 to 10 times by weight the total quantity of hydrocarbon blend prevalently consisting of dimethylnaphthalene isomers left to crystallize and preferably said quantity of low molecular weight alcohol ranges from 0.1 to 10 times the quantity of hydrocarbon blend left to crystallize. The washing phase $E_b$ of the precipitate thus obtained is carried out by re-dispersion of the solid, obtained from the crystallization after separation of the remaining mother liquor liquid phase, in a low molecular weight alcohol and the subsequent separation of the solid until a residual content of mother liquor of the previous crystallization is obtained, not higher than 30% by weight of the total quantity of solid plus the wetting mother liquor and preferably not higher than 10% by weight of said quantity.

The re-crystallization phase $E_c$ of the precipitate obtained from the previous washing phase is carried out in the presence of a low molecular weight alcohol, preferably selected from methanol, ethanol, propanol and glycols, more preferably methanol, using a quantity of said alcohol at least equal to the minimum quantity necessary for the dissolution of said precipitate at a temperature ranging from room temperature to 120° C. and more preferably at a temperature ranging from 50 to 120° C. and subsequently proceeding with the re-crystallization by cooling the solution thus obtained and/or by evaporation of the alcohol solvent used, under static conditions or under stirring. Said re-crystallization phase can also be carried out using a lower quantity of alcohol solvent than the minimum amount necessary for the dissolution of the precipitate obtained from the previous washing phase, preferably using a quantity of alcohol ranging from 20% to 80% of said minimum quantity, operating at a temperature ranging from room temperature to 120° C. and more preferably at a temperature ranging from 50 to 120° C., maintaining the system under stirring for a certain period of time and subsequently proceeding with the re-crystallization phase starting from an alcohol mixture in which part of the starting precipitate obtained from the previous washings is still present.

The re-crystallization phase in which the quantity of alcohol solvent used is lower than the minimum amount necessary for the complete dissolution of the precipitate, can also be carried out by subjecting the alcohol dispersion containing part of the precipitate to one or more cooling and heating cycles before proceeding with the re-crystallization according to what has already been described above.

The precipitate obtained from said re-crystallization phase is separated from the liquid phase, prevalently consisting of the low molecular weight alcohol used, by means of conventional decanting, centrifugation, filtration and final evaporation methods, optionally under vacuum to eliminate the residual solvent, in order to obtain the 2,6-dimethylnaphthalene isomer with a very high purity degree, in any case with a purity not lower than 99% of 2,6-dimethylnaphthalene.

Some examples are provided below for the sole purpose of better illustrating the invention without, however, limiting its scope.

EXAMPLE 1

STEP F

A catalytic transformation test of polynaphthalene blends is carried out to obtain the production of naphthalene and methylnaphthalenes, in the presence of a blend of benzene hydrocarbons and hydrogen and a catalyst containing ZSM-12 zeolite the same as the catalyst described in Example 2 of patent application US 2003/0069459 A1 and prepared according to the procedure described in said example.

The experimental device used consists of a tank containing the blend of polynaphthalenes and benzene hydrocarbons to be reacted, a feeding pump for sending the mixture to an AISI 316 tubular steel reactor having an internal diameter equal to 3.4 cm and a length equal to 50 cm equipped with an electric heating jacket, a pressure regulation valve situated at the outlet of the reactor, a collection tank of the reaction effluent. The experimental device described is also equipped with a mass flow-rate controller for sending the hydrogen to the reactor.

The conditions under which the catalytic test is carried out are as follows:
Quantity of catalyst in the reactor equal to 190 g
Hourly flow-rate of the blend (polymethylnaphthalenes+benzene hydrocarbon) fed to the reactor equal to 102 g/h
Hourly flow-rate of the hydrogen fed to the reactor equal to 2.14 g/h
Weight composition of the blend fed equal to 18.8% of dimethylnaphthalenes, 4.8% of polymethylnaphthalenes, from trimethylnaphthalenes to pentamethylnaphthalenes, 74.7% of benzene hydrocarbons (benzene+toluene+xylenes+trimethylbenzenes+tetramethylbenzenes+pentamethylbenzene) having an overall ratio between methyl benzenes and benzene rings equal to 1.15. The blend fed to the reactor therefore has an overall ratio between benzene compounds and naphthalene compounds equal to 5 molar.
The temperature at which the reactor is set is equal to 355° C. with a shift equal to about 1° C. along the whole greater axis of the reactor itself.
the pressure at which the reactor is set is equal to 60 bar.

The test is activated by bringing the reactor to the reaction temperature by electric heating and feeding the reaction mixture at the flow-rate indicated when the temperature of the reactor, during the progressive heating, reaches approximately 200° C. The reaction effluent is only considered as being representative of the test when the temperature inside the reactor has stably reached a value equal to 355° C.

Analyses are then effected on samples of reaction effluent obtained at increasing time-on-stream values. The results of these analyses allow the performances of the reactor to be calculated as the test proceeds as indicated in the following table, wherein:
C=Molar conversion percentage of (dimethylnaphthalenes+polymethylnaphthalenes)
S=Molar selectivity percentage to (naphthalene+monomethylnaphthalenes) with respect to (dimethylnaphthalenes+polymethylnaphthalenes)
BS=Material balance percentage referring to the benzene compounds alone: (benzene compounds at the outlet)/(benzene compounds fed) wherein "benzene compounds" refers to the overall quantity by weight of (benzene+toluene+xylenes+trimethylbenzenes+tetramethylbenzenes+pentamethylbenzenes)
BN=Material balance percentage referring to the naphthalene compounds alone: (naphthalene compounds at the outlet)/(naphthalene compounds fed) wherein "naphthalene compounds" refers to the overall quantity by weight of (naphthalene+monomethylnaphthalenes+dimethylnaphthalenes+trimethylnaphthalenes+tetramethylnaphthalenes).
R=C*S=Yield to (naphthalene+monomethylnaphthalenes)

| Running hours | C | S | BS | BN | R = C * S |
|---|---|---|---|---|---|
| 19 | 28.0 | 55.7 | 100.0 | 89.4 | 15.6 |
| 94 | 26.1 | 63.3 | 99.6 | 92.2 | 16.5 |
| 115 | 26.3 | 62.7 | 99.7 | 92.0 | 16.5 |
| 139 | 24.5 | 65.8 | 99.8 | 93.3 | 16.1 |
| 170 | 23.9 | 67.9 | 99.7 | 94.0 | 16.2 |
| 187 | 23.3 | 70.4 | 99.8 | 94.8 | 16.4 |
| 194 | 23.8 | 68.5 | 99.6 | 94.2 | 16.3 |
| 216 | 23.3 | 69.8 | 99.7 | 94.6 | 16.3 |

The data indicated in the table show that the yield to (naphthalene+monomethylnaphthalenes) reaches a stable value, after about 100 hours of reaction, approximately within the range of 16.1 to 16.4%. This is actually due to the combined effect of a modest loss in activity of the catalyst as the test proceeds (as the conversion value shows) and a contemporaneous increase in the selectivity to the products of interest.

The data relating to the material balance of the benzene component (BS) and the material balance of the naphthalene component (BN) show that the blend of benzene hydrocarbons is not substantially used up during the reaction, whereas the naphthalenes undergo a minimum degradation to non-naphthalene products.

It is evident that in a chemical process characterized by the necessary recycling of both the non-converted naphthalene reagent and the blend of benzene hydrocarbons, it is preferable, in order to minimize the specific consumptions of both the naphthalene reagent and blend of benzene hydrocarbons, to have material balances which are as high as possible per passage.

EXAMPLE 2

Comparative (Step F without Hydrogen)

Step 1 is repeated in the absence of hydrogen.

The same catalytic test is carried out in the same experimental device already described in example 1, for the transformation of polymethyl naphthalene blends in order to obtain the production of naphthalene and methyl naphthalenes, in the presence of the same blend of benzene hydrocarbons and of the same catalyst based on ZSM-12 zeolite already used in the previous example 1, but in the absence of hydrogen.

The experimental conditions used, as well as the operative method, with the exception of the above-mentioned absence of hydrogen, are completely analogous to those used in the test of example 1.

A single sampling of reaction effluent is effected after 142 hours of continuous running, under the conditions indicated, and on which the gas-chromatographic analysis is carried out.

The result of this analysis allows the performances of the reactor to be calculated, under steady conditions, as shown in the following table where the performances are expressed as "IC", "S", "BN", "BS" and R analogously to what is already defined in example 1.

| Running hours | C | S | BS | BN | R = C * S |
|---|---|---|---|---|---|
| 142 | 27.1 | 40.3 | 95.1 | 85.1 | 10.9 |

The data shown in the table demonstrate that the yield to (naphthalene+monomethyl naphthalenes) is lower than the quantity obtained in the test described in the previous example 1. The data of the solvent material balance (BS) and of the material balance of the naphthalene reagent (BN) prove to be lower than the same data obtained in example 1.

The data relating to the material balance of the benzene component (BS) and to the material balance of the naphthalene component (BN) demonstrate that, in this case, both the benzene hydrocarbons and the naphthalenes are more degradated with respect to what is indicated in example 1.

It is evident that in a chemical process characterized by the necessary recycling of both the non-converted naphthalene reagent and the blend of benzene hydrocarbons, in order to minimize the specific consumptions of the naphthalene reagent and the benzene hydrocarbon blend, it is preferable to have the highest possible material balances per passage.

By comparing the data obtained in this example with the data already obtained in example 1, the positive effect of hydrogen in diminishing the entity of degradation reactions and consumption, both of the benzene hydrocarbon blend and naphthalene reagent, is clearly evident.

Particularly positive is the balance of the benzene hydrocarbon blend (BS), obtained in the presence of hydrogen, with respect to what was obtained in the absence of hydrogen—all the other experimental conditions being the same—in relation to the excess of benzene hydrocarbons present in the system with respect to the naphthalene reagent. Under the effective recycling conditions of the non-converted naphthalene reagent and benzene hydrocarbon blend, i.e. under the real conditions of a chemical process on an industrial scale, the loss of a few percentage points in the balance of the benzene hydrocarbon blend is much more penalizing with respect to an analogous loss in the balance of the naphthalene reagent.

The invention claimed is:

1. A process for the production of 2,6-dimethylnaphthalene starting from hydrocarbon blends containing naphthalene and/or methyl naphthalene isomers and/or dimethyl naphthalene isomers and/or polymethyl naphthalene isomers, one or more benzene hydrocarbons, optionally a methylating agent, in the presence of a zeolite catalyst belonging to the MTW structural group, comprising the following steps:

I. A first chemical transformation I of naphthalene blends containing naphthalene and/or methyl naphthalene isomers and/or dimethyl naphthalene isomers and/or polymethyl naphthalene isomers, effected in the presence of one or more benzene hydrocarbons, a catalyst containing a zeolite belonging to the MTW structural group, optionally a methylating agent, with the aim of producing a naphthalene blend enriched in the 2,6-dimethylnaphthalene isomer, wherein the benzene hydrocarbon is selected from benzene, toluene, xylene isomers, trimethyl benzene isomers, tetramethyl benzene isomers, pentamethyl benzene, hexamethyl benzene and blends thereof, and the overall ratio between the number of moles of methyl radicals contained in the benzene hydrocarbons and the number of moles of benzene rings is higher than the overall ratio between the number of moles of methyl radicals contained in the naphthene hydrocarbons and the number of moles of naphthalene rings of the naphthalene fraction reacted, II. A second chemical transformation II of naphthalene blends mainly containing dimethyl naphthalene isomers and/or polymethyl naphthalene isomers, effected in the presence of a catalyst containing a zeolite belonging to the MTW structural group, and one or more benzene hydrocarbons selected from benzene, toluene, xylene isomers, trimethyl benzene isomers, tetramethyl benzene isomers, pentamethyl benzene, hexamethyl benzene and blends thereof, and the overall ratio between the number of moles of methyl radicals contained in the benzene hydrocarbons and the number of moles of benzene aromatic rings is lower than the overall ratio between the number of moles of methyl radicals contained in the naphthene substrate and the number of moles of naphthalene rings of the naphthalene fraction reacted, with the aim of obtaining a naphthalene blend containing a higher concentration of naphthalene and methyl naphthalenes with respect to the blend reacted, wherein said naphthalene and methyl naphthalenes are re-used in step I;

III. Optionally a third chemical transformation III of naphthalene blends mainly containing dimethyl naphthalene isomers, effected in the absence of benzene hydrocarbons and in the presence of a catalyst containing a zeolite belonging to the MTW structural group, with the aim of obtaining a blend of dimethyl naphthalene isomers, enriched in the 2,6-dimethylnaphthalene isomer, wherein hydrogen is fed in the chemical transformation step I and/or in the chemical transformation step II.

2. The process according to claim 1, further comprising at least one separation step, by distillation, of the blends resulting from the chemical transformations and at least one purification phase, by means of crystallization operations and washings, of the blends resulting from the chemical transformations.

3. The process according to claim 1, wherein the naphthalene blends which are subjected to chemical transformation in step I derive from a treatment comprising the following steps:

A. Separation by distillation of a hydrocarbon blend, containing, among other products, naphthalene and/or methylnaphthalene isomers and/or dimethylnaphthalene isomers and/or polymethylnaphthalene isomers in order to obtain a first hydrocarbon fraction characterized by a higher concentration of said naphthalene compounds with respect to the initial hydrocarbon blend and a second fraction prevalently consisting of non-naphthalene compounds, wherein the first fraction is sent to the subsequent step B;

B. Treatment of the first fraction obtained in step A by reaction of said fraction with a solid acid catalyst, optionally in the presence of a hydrocarbon or blend of benzene hydrocarbons, and separation by distillation of the hydrocarbon blend effluent from said treatment, in order to obtain a first hydrocarbon fraction consisting of said naphthalene compounds and possibly the hydrocarbon or blend of benzene hydrocarbons, and a second hydrocarbon fraction prevalently containing non-naphthalene compounds, wherein the first fraction is fed to step I.

4. The process according to claim 1, wherein the naphthalene blend resulting from the chemical transformation I is subjected to one or more separation steps obtaining several fractions, among which a fraction with a higher concentration of the 2,6-dimethylnaphthalene isomer, possibly a fraction with a higher concentration of the 1,6 and 1,5-dimethyl naphthalene isomers to be used as feed to step III, and at least a fraction containing mainly dimethyl naphthalenes and/or polymethyl naphthalenes to be used as feed to step II.

5. The process according to claim 1, wherein the naphthalene blend resulting from the chemical transformation II is subjected to one or more separation steps obtaining several fractions, among which a fraction containing naphthalene and methyl naphthalenes which is sent to step I.

6. The process according to claim 1, containing the following steps and in which hydrogen is fed in step C and/or F:

A. Separation by distillation of a hydrocarbon blend, containing, among other products, naphthalene and/or methylnaphthalene isomers and/or dimethylnaphthalene isomers and/or polymethylnaphthalene isomers in order to obtain a first hydrocarbon fraction characterized by a higher concentration of said naphthalene compounds with respect to the initial hydrocarbon blend and a second fraction prevalently consisting of non-naphthalene compounds, wherein the first fraction is sent to the subsequent step B whereas the second fraction leaves the process;

B. Treatment of the first fraction obtained in step A by reaction of said fraction with a solid acid catalyst, optionally in the presence of a hydrocarbon or blend of benzene hydrocarbons, and separation by distillation of the hydrocarbon blend effluent from said treatment, in order to obtain a first hydrocarbon fraction consisting of said naphthalene compounds and possibly the hydrocarbon or blend of benzene hydrocarbons, sent to the subsequent step C, and a second hydrocarbon fraction prevalently containing heavy non-naphthalene compounds, which leaves the process;

C. Chemical transformation I of the first fraction obtained in step B and the second fraction obtained in step D, containing as a whole naphthalene and/or methylnaphthalene isomers and/or dimethylnaphthalene isomers and/or polymethylnaphthalene isomers, in a hydrocarbon blend effluent from said step C enriched with 2,6 dimethylnaphthalene isomer, wherein said chemical transformation I is carried out in the presence of one or more benzene hydrocarbons, a solid acid catalyst containing a MTW zeolite, and an inorganic binder, and optionally in the presence of a methylating agent;

D. Separation by distillation of the hydrocarbon blend effluent from step C and subsequent step G, containing an aqueous phase, one or more benzene hydrocarbons, naphthalene and/or methylnaphthalene isomers and/or dimethylnaphthalene isomers and/or polymethylnaphthalene isomers in order to obtain:

a first fraction prevalently consisting of water and a blend of benzene hydrocarbons prevalently containing benzene, toluene and xylenes having an overall molar ratio between methylbenzenes and benzene rings lower than or equal to 2, wherein said fraction, after separation and removal by de-mixing of the aqueous phase, is partly sent to step B and partly to the subsequent step F;

a second fraction prevalently consisting of (1) a hydrocarbon or blend of prevalently tri-, tetra-, penta-benzene hydrocarbons and hexamethylbenzene, and possibly xylenes, having an overall molar ratio between benzene methyls and benzene rings higher than 2, 2) naphthalene, 3) methylnaphthalene isomers, wherein said second fraction is sent to the previous step C;

a third fraction prevalently consisting of dimethylnaphthalene isomers, including the 2,6 dimethylnaphthalene isomer, which is sent to the subsequent step H;

a fourth fraction prevalently consisting of tri-, tetra-, penta- and hexamethylnaphthalenes, which is sent to the subsequent step F;

E. Purification of the first fraction, obtained from the subsequent step H, and prevalently consisting of a blend of dimethylnaphthalene isomers characterized by a high concentration of the 2,6-dimethylnaphthalene isomer and a low concentration of the 1,6- and 1,5-dimethylnaphthalene isomers, by means of crystallization steps by cooling, subsequent washings and re-crystallizations effected in the presence of a low molecular weight alcohol selected from methanol, ethanol and propanol, to obtain a first fraction consisting of 2,6-dimethylnaphthalene with a very high degree of purity, which forms the desired end-product, and a second fraction prevalently consisting of dimethylnaphthalene isomers, comprising the 2,6-dimethylnaphthalene isomer, wherein said second fraction obtained in the present step E is sent to the subsequent step F;

F. Chemical transformation II of the hydrocarbon blend prevalently containing dimethylnaphthalene isomers and/or polymethylnaphthalene isomers greater than dimethylnaphthalene, carried out in the presence of a solid acid catalyst, containing a MTW zeolite, and an inorganic binder, and a hydrocarbon or blend of benzene hydrocarbons so that the overall molar ratio between the methylbenzenes and benzene rings is lower than or equal to 2, in order to obtain a hydrocarbon blend, effluent from said step F, having a higher concentration of naphthalene and methylnaphthalenes with respect to the total blend reacted, and wherein said blend is sent to the subsequent step G;

G. Separation by distillation of a hydrocarbon blend containing a hydrocarbon or blend of benzene hydrocarbons, naphthalene and/or methylnaphthalene isomers and/or dimethylnaphthalene isomers and/or polymethylnaphthalene isomers obtained in the previous step F, to obtain:

a first fraction consisting of a hydrocarbon or blend of benzene hydrocarbons, naphthalene and methylnaphthalene isomers, which is sent to the separation step D, a second fraction prevalently consisting of dimethylnaphthalene isomers, comprising the 2,6-dimethylnaphthalene isomer, and polymethylnaphthalenes, which is sent, totally, or partially, to the chemical transformation step F;

H. Separation, by distillation, of a hydrocarbon blend prevalently consisting of dimethylnaphthalene isomers in order to obtain:

a first fraction prevalently consisting of dimethylnaphthalene isomers with a higher concentration of the 2,6-dimethylnaphthalene isomer and a lower concentration of 1,6- and 1,5-dimethylnaphthalene isomers, with respect to the initial concentrations of the mixture fed in the present step, which is sent to the previous step E;

a second fraction prevalently consisting of dimethylnaphthalene isomers with a lower concentration of the 2,6-dimethylnaphthalene isomer and a higher concentration of 1,6- and 1,5-dimethylnaphthalene isomers, with respect to the initial concentrations of the mixture fed in the present step, which is sent to the subsequent step J;

J. Chemical transformation III of a hydrocarbon blend prevalently consisting of dimethylnaphthalene, obtained as second fraction of the previous step H, carried out in the presence of a catalyst containing a MTW zeolite, and an inorganic binder, in order to obtain a hydrocarbon blend, effluent of said step J, having a higher concentration of the 2,6-dimethylnaphthalene isomer with respect to the concentration of the mixture fed to said step J, which is totally or partially sent back to step H.

7. The process according to claim 1, wherein the chemical transformation I is effected in the presence of one or more benzene hydrocarbons which have an overall ratio between the number of moles of methyl radicals contained in the benzene aromatic hydrocarbons and the number of moles of benzene aromatic rings, equal to or higher than 2.

8. The process according to claim 7, wherein the overall ratio between the number of moles of methyl radicals contained in the benzene aromatic hydrocarbons and the number of moles of benzene aromatic rings, is equal to or higher than 3.

9. The process according to claim 1, wherein hydrogen is fed at least to the chemical transformation step II.

10. The process according to claim 9, wherein hydrogen is fed to the chemical transformation step II only.

11. The process according to claim 6, containing the following steps and wherein hydrogen is fed to step F only:

A. Separation by distillation of a hydrocarbon blend, containing, among other products, naphthalene and/or methylnaphthalene isomers and/or dimethylnaphthalene isomers and/or polymethylnaphthalene isomers in order to obtain a first hydrocarbon fraction characterized by a higher concentration of said naphthalene compounds with respect to the initial hydrocarbon blend and a second fraction prevalently consisting of non-naphthalene compounds, wherein the first fraction is sent to the subsequent step B whereas the second fraction leaves the process;

B. Treatment of the first fraction obtained in step A by reaction of said fraction with a solid acid catalyst, optionally in the presence of a hydrocarbon or blend of benzene hydrocarbons, and separation by distillation of the hydrocarbon blend effluent from said treatment, in order to obtain a first hydrocarbon fraction consisting of said naphthalene compounds and possibly the hydrocarbon or blend of benzene hydrocarbons, sent to the subsequent step C, and a second hydrocarbon fraction prevalently containing heavy non-naphthalene compounds, which leaves the process;

C. Chemical transformation I of the first fraction obtained in step B and the second fraction obtained in step D, containing as a whole naphthalene and/or methylnaphthalene isomers and/or dimethylnaphthalene isomers and/or polymethylnaphthalene isomers, in a hydrocarbon blend effluent from said step C enriched with 2,6 dimethylnaphthalene isomer, wherein said chemical transformation I is carried out in the presence of one or more benzene hydrocarbons, which have an overall ratio between the number of moles of methyl radicals contained in the benzene aromatic hydrocarbons and the number of moles of benzene aromatic rings equal to or higher than 2, a solid acid catalyst containing a MTW zeolite, an inorganic binder, and in the presence of a methylating agent;

D. Separation by distillation of the hydrocarbon blend effluent from step C and subsequent step G, containing an aqueous phase, one or more benzene hydrocarbons, naphthalene and/or methylnaphthalene isomers and/or dimethylnaphthalene isomers and/or polymethylnaphthalene isomers in order to obtain:
  a first fraction prevalently consisting of water and a blend of benzene hydrocarbons prevalently containing benzene, toluene and xylenes having an overall molar ratio between methylbenzenes and benzene rings lower than or equal to 2, wherein said fraction, after separation and removal by de-mixing of the aqueous phase, is partly sent to step B and partly to the subsequent step F;
  a second fraction prevalently consisting of (1) a hydrocarbon or blend of prevalently tri-, tetra-, pentabenzene hydrocarbons and hexamethylbenzene, and possibly xylenes, having an overall molar ratio between benzene methyls and benzene rings higher than 2, 2) naphthalene, 3) methylnaphthalene isomers, wherein said second fraction is sent to the previous step C;
  a third fraction prevalently consisting of dimethylnaphthalene isomers, including the 2,6 dimethylnaphthalene isomer, which is sent to the subsequent step H;
  a fourth fraction prevalently consisting of tri-, tetra-, penta- and hexamethylnaphthalenes, which is sent to the subsequent step F;

E. Purification of the first fraction, obtained from the subsequent step H, and prevalently consisting of a blend of dimethylnaphthalene isomers characterized by a high concentration of the 2,6-dimethylnaphthalene isomer and a low concentration of 1,6- and 1,5-dimethylnaphthalene isomers, by means of crystallization steps by cooling, subsequent washings and re-crystallizations effected in the presence of a low molecular weight alcohol selected from methanol, ethanol and propanol, to obtain a first fraction consisting of 2,6-dimethylnaphthalene with a very high degree of purity, which forms the desired end-product, and a second fraction prevalently consisting of dimethylnaphthalene isomers, comprising the 2,6-dimethylnaphthalene isomer, wherein said second fraction obtained in the present step E is sent to the subsequent step F;

F. Chemical transformation II of the hydrocarbon blend prevalently containing dimethylnaphthalene isomers and/or polymethylnaphthalene isomers greater than dimethylnaphthalene, carried out in the presence of a solid acid catalyst, containing a MTW zeolite, and an inorganic binder, and a hydrocarbon or blend of benzene hydrocarbons so that the overall molar ratio between the methylbenzenes and benzene rings is lower than or equal to 2, in order to obtain a hydrocarbon blend, effluent from said step F, having a higher concentration of naphthalene and methylnaphthalenes with respect to the total blend reacted, and wherein said blend is sent to the subsequent step G;

G. Separation by distillation of a hydrocarbon blend containing a hydrocarbon or blend of benzene hydrocarbons, naphthalene and/or methylnaphthalene isomers and/or dimethylnaphthalene isomers and/or polymethylnaphthalene isomers obtained in the previous step F, to obtain:
  a first fraction consisting of a hydrocarbon or blend of benzene hydrocarbons, naphthalene and methylnaphthalene isomers, which is sent to the separation step D;
  a second fraction prevalently consisting of dimethylnaphthalene isomers, comprising the 2,6-dimethylnaphthalene isomer, and polymethylnaphthalenes, which is sent, totally or partially, to the chemical transformation step F;
  a third fraction essentially consisting of hydrogen which can be re-used in step F;

H. Separation, by distillation, of a hydrocarbon blend prevalently consisting of dimethylnaphthalene isomers in order to obtain:
  a first fraction prevalently consisting of dimethylnaphthalene isomers with a higher concentration of the 2,6-dimethylnaphthalene isomer and a lower concentration of 1,6- and 1,5-dimethylnaphthalene isomers, with respect to the initial concentrations of the mixture fed in the present step, which is sent to the previous step E;
  a second fraction prevalently consisting of dimethylnaphthalene isomers with a lower concentration of the 2,6-dimethylnaphthalene isomer and a higher concentration of 1,6- and 1,5-dimethylnaphthalene isomers, with respect to the initial concentrations of the mixture fed in the present step, which is sent to the subsequent step J;

J. Chemical transformation III of a hydrocarbon blend prevalently consisting of dimethylnaphthalene, obtained as second fraction of the previous step H, carried out in the presence of a catalyst containing a MTW zeolite, and an inorganic binder, in order to obtain a hydrocarbon blend, effluent of said step J, having a higher concentration of the 2,6-dimethylnaphthalene isomer with respect to the concentration of the mixture fed to said step J, which is totally or partially sent back to step H.

12. The process according to claim 1, wherein the naphthalene hydrocarbon blend used in the chemical transformation I contains mainly naphthalene and monomethylnaphthalene.

13. The process according to claim 1, wherein the benzene hydrocarbon used in the chemical transformation I is toluene, xylene or 1,2,4-trimethylbenzene or blends thereof.

14. The process according to claim 1, wherein, in the chemical transformation step II, the hydrocarbon or the blend of benzene hydrocarbons has an overall ratio between the number of moles of methyl radicals and the number of moles of aromatic rings, equal to or lower than 2.

15. The process according to claim 1, wherein in the chemical transformation step I, the operation is effected in the presence of a methylating agent.

16. The process according to claim 15, wherein the methylating agent is methanol.

17. The process according to claim 1, wherein the MTW zeolite used in the chemical transformations I, II and III is a ZSM-12 zeolite.

18. The process according to claim 1, wherein the MTW zeolite is a silico-aluminate with an $SiO_2/Al_2O_3$ molar ratio higher than or equal to 20.

19. The process according to claim 18, wherein the $SiO_2/Al_2O_3$ molar ratio is higher than 70.

20. The process according to claim 1, wherein the MTW zeolite is used in the form in which the cationic sites present in the structure are occupied for at least 50% by hydrogen ions.

21. The process according to claim 20, wherein the cationic sites are occupied for at least 90% by hydrogen ions.

22. The process according to claim 1, wherein the MTW zeolite is used in a form bound by a binder.

23. The process according to claim 22, wherein the binder is selected from alumina, silica, a silico-aluminate, titania, zirconia or clay.

24. The process according to claim 22, wherein the catalytic compositions containing MTW zeolite and the binder have an extra-zeolite porosity not lower than 0.4 ml/g of catalyst and a fraction equal to at least 50% of said extra-zeolite porosity is characterized by pores having a diameter larger than 100 Angstrom.

25. The process according to claim 1, wherein hydrogen is fed to the chemical transformation step I and the molar ratio in said step between the hydrocarbon or the blend of benzene hydrocarbons and the hydrocarbon or blend of naphthalene hydrocarbons, ranges from 1 to 10.

26. The process according to claim 1, wherein hydrogen is fed to the chemical transformation step II and the molar ratio in said step between the hydrocarbon or the blend of benzene hydrocarbons and the hydrocarbon or blend of naphthalene hydrocarbons, ranges from 1 to 10.

27. The process according to claim 25, wherein the molar ratio between the hydrocarbon or the blend of benzene hydrocarbons and the hydrocarbon or blend of naphthalene hydrocarbons, ranges from 1 to 5.

28. The process according to claim 27, wherein the molar ratio between the hydrocarbon or the blend of benzene hydrocarbons and the hydrocarbon or blend of naphthalene hydrocarbons, is higher than or equal to 2 and lower than 5.

29. The process according to claim 1, wherein a ethylating agent is used in the chemical transformation step 1 and the molar ratio used between the methylating agent and the hydrocarbon or the blend of naphthalene hydrocarbons is lower than 30.

30. The process according to claim 29, wherein the molar ratio used between the methylating agent and the hydrocarbon or the blend of naphthalene hydrocarbons ranges from 0.1 to 3.

31. The process according to claim 1, wherein the chemical transformation step I is carried out at a temperature ranging from 150 to 450° C. and at a pressure ranging from 3 to 60 absolute bar.

32. The process according to claim 1, wherein the chemical transformation step II is carried out at a temperature ranging from 150 to 450° C. and at a pressure ranging from 3 to 60 absolute bar.

33. The process according to claim 1, wherein the chemical transformation step III is present and is carried out at a temperature ranging from 150 to 450° C. and at a pressure ranging from 3 to 60 absolute bar.

34. The process according to claims claim 31, wherein the combination of the temperature and pressure conditions independently adopted in the chemical transformation steps I, II and III, is selected so that each chemical transformation is effected, at least partially, in liquid phase.

35. The process according to claim 34, wherein each chemical transformation I, II and III is effected under completely liquid phase conditions.

36. The process according to claim 1, wherein the chemical transformation step I is effected in the presence of hydrogen and the molar ratio between the hydrogen and the hydrocarbon or blend of naphthalene hydrocarbons ranges from 0.1 to 100.

37. The process according to claim 1, wherein the chemical transformation step II is effected in the presence of hydrogen and the molar ratio adopted in the chemical transformation step II between the hydrogen and the hydrocarbon or blend of naphthalene hydrocarbons ranges from 0.1 to 100.

38. The process according to claim 36, wherein the molar ratio between hydrogen and the hydrocarbon or the blend of naphthalene hydrocarbons ranges from 0.5 to 10.

39. The process according to claim 1 herein step I of the chemical transformation I is effected by adopting 4 reaction steps in series, to the first of which all the hydrocarbon or blend of benzene hydrocarbons, and optionally hydrogen when present, are fed, according to the reaction conditions selected, together with a first portion of the hydrocarbon or blend of naphthalene hydrocarbons, the remaining portions of hydrocarbon or blend of naphthalene hydrocarbons are fed to the second and third step, whereas the whole quantity of methylating agent envisaged is fed to the fourth step.

40. The process according to claim 39, wherein the WHSV space velocity expressed as kg of charge fed/hour/kg of catalyst present in the 4 reaction steps, ranges from 0.1 to 8 hours$^{-1}$.

41. The process according to claim 40, wherein the space velocity ranges from 0.5 to 4 hours$^{-1}$.

42. The process according to claim 1, wherein in the chemical transformation step II the operations are effected by adopting 4 reaction steps in series, to the first of which all the hydrocarbon or blend of benzene hydrocarbons, and optionally hydrogen when present, are fed, according to the reaction conditions selected, together with a first portion of the hydrocarbon or blend of naphthalene hydrocarbons, the remaining portions of hydrocarbon or blend of naphthalene hydrocarbons are fed to the remaining catalytic steps.

43. The process according to claim 1, wherein once the MTW zeolite is exhausted, it is regenerated by treatment, under at least partially liquid phase conditions, with one or more benzene hydrocarbons selected from benzene, toluene, xylene isomers, trimethyl benzene isomers, tetramethyl benzene isomers, pentamethethyl benzene, hexamethyl benzene, at a temperature ranging from 200° C. to 450° C. and at least equal to the temperature used in the specific chemical transformation step I, II or III, from which the exhausted zeolite derives, at a pressure ranging from 3 to 60 absolute bar and at a WHSV, as described above, from 0.1 to 8 hours$^{-1}$.

44. The process according to claim 3, wherein in step A hydrocarbon blends are fed, containing naphthalene hydrocarbons coming from the fractioning of petrochemical or refinery streams.

45. The process according to claim 44 wherein cracking oils called FOK and LCO are used as the feed to step A.

46. The process according to claim 3, wherein in step B, a continuous, semi-continuous or batch operation is effected by feeding the concentrated naphthalene stream to a reactor containing the solid acidic catalyst, under at least partial liquid phase conditions, at a temperature ranging from room temperature to 360° C.

47. The process according to claim 46, wherein in step B, batch or semi-continuous operations are effected and the quantity of acidic solid ranges from 0.1% to 5% by weight with respect to the hydrocarbon blend to be treated coming from step A, for a treatment time not longer than 5 minutes.

48. The process according to claim 46, wherein in step B continuous operations are effected and the hydrocarbon blend coming from step A is fed to step B with a WHSV ranging from 0.1 to 6 hours$^{-1}$.

49. The process according to claim 3, wherein the concentrated naphthalene stream obtained in step A is fed to the treatment B after dilution with one or more benzene hydrocarbons selected from benzene, toluene, xylene isomers, trimethyl benzene isomers, tetramethyl benzene isomers, pentamethyl benzene, hexamethyl benzene.

50. The process according to claim 3, wherein in step B the solid acid catalysts are selected from clays, phyllo-silicates, acid or partially acid zeolites, sulphated zirconia, acid resins, alumina, activated aluminas, amorphous silico-aluminas, acid oxides in general, partially salified heteropoly acids and supported acids.

51. The process according to claim 31, wherein the temperature ranges from 200 to 450° C.

52. The process according to claim 51, wherein the temperature ranges from 300 to 400° C.

53. The process according to claim 32, wherein the temperature ranges from 200 to 450° C.

54. The process according to claim 53, wherein the temperature ranges from 300 to 400° C.

55. The process according to claim 33, wherein the temperature ranges from 150 to 400° C.

56. The process according to claim 55, wherein the temperature ranges from 200 to 350° C.

57. The process according to claim 1, wherein the overall flow-rate of the reactants fed in the chemical transformation steps I and/or II, expressed as WHSV ranges from 0.1 to 8 hours$^{-1}$.

58. The process according to claim 57, wherein the WHSV ranges from 0.5 to 4 hours$^{-1}$.

59. The process according to claim 1, wherein the overall flow-rate of the reactants fed in the chemical transformation step III, expressed as iSV, ranges from 0.01 to 20 hours$^{-1}$.

60. The process according to claim 59, wherein the WHSV, ranges from 4 to 16 hours$^{-1}$.

61. A process for the preparation of 2,6-dimethyl naphthalene which comprises reacting naphthalene blends containing naphthalene and/or methyl naphthalene isomers and/or dimethyl naphthalene isomers and/or polymethyl naphthalene isomers, in the presence of hydrogen, of one or more benzene hydrocarbons, a catalyst containing a zeolite belonging to the MTW structural group, and optionally a methylating agent, with the aim of producing a naphthalene blend enriched in the 2,6-dimethylnaphthalene isomer, wherein the benzene hydrocarbon is selected from benzene, toluene, xylene isomers, trimethyl benzene isomers, tetramethyl benzene isomers, pentamethyl benzene, hexamethyl benzene and blends thereof and the overall ratio between the number of moles of methyl radicals contained in the benzene hydrocarbons and the number of moles of benzene rings is higher than the overall ratio between the number of moles of methyl radicals contained in the naphthalene hydrocarbons and the number of moles of naphthalene rings, of the naphthalene fraction reacted.

62. The process according to claim 26, wherein the molar ratio between the hydrocarbon or the blend of benzene hydrocarbons and the hydrocarbon or blend of naphthalene hydrocarbons, ranges from 1 to 5.

63. The process according to claim 62, wherein the molar ratio between the hydrocarbon or the blend of benzene hydrocarbons and the hydrocarbon or blend of naphthalene hydrocarbons, is higher than or equal to 2 and lower than 5.

64. The process according to claim 32, wherein the combination of the temperature and pressure conditions independently adopted in the chemical transformation steps I, II and III, is selected so that each chemical transformation is effected, at least partially, in liquid phase.

65. The process according to claim 64, wherein each chemical transformation I, II and III is effected under completely liquid phase conditions.

66. The process according to claim 3, wherein the combination of the temperature and pressure conditions independently adopted in the chemical transformation steps I, II and III, is selected so that each chemical transformation is effected, at least partially, in liquid phase.

67. The process according to claim 66, wherein each chemical transformation I, II and III is effected under completely liquid phase conditions.

68. The process according to claim 37, wherein the molar ratio between hydrogen and the hydrocarbon or the blend of naphthalene hydrocarbons ranges from 0.5 to 10.

* * * * *